(12) United States Patent
Nazarifar et al.

(10) Patent No.: US 8,006,570 B2
(45) Date of Patent: Aug. 30, 2011

(54) NON-INVASIVE FLOW MEASUREMENT

(75) Inventors: Nader Nazarifar, Laguna Niguel, CA (US); Laurens J. Drost, Ithaca, NY (US); Yuri M. Shkarlet, Pompano Beach, FL (US)

(73) Assignee: Alcon, Inc., Hunenberg (CH)

( * ) Notice: Subject to any disclaimer, the term of this patent is extended or adjusted under 35 U.S.C. 154(b) by 1273 days.

(21) Appl. No.: 11/523,272

(22) Filed: Sep. 19, 2006

(65) Prior Publication Data
US 2007/0244427 A1 Oct. 18, 2007

Related U.S. Application Data

(63) Continuation-in-part of application No. 11/391,748, filed on Mar. 29, 2006.

(51) Int. Cl.
*G01F 1/66* (2006.01)
*A61M 1/00* (2006.01)
*A61B 8/00* (2006.01)

(52) U.S. Cl. .................. 73/861.25; 604/30; 600/437
(58) Field of Classification Search .............. 604/30, 604/131; 73/861.25–861.31; 600/437
See application file for complete search history.

(56) References Cited

U.S. PATENT DOCUMENTS

| | | |
|---|---|---|
| 4,395,258 A | 7/1983 | Wang et al. |
| 4,479,761 A | 10/1984 | Bilstad et al. |
| 4,493,695 A | 1/1985 | Cook |
| 4,592,741 A | 6/1986 | Vincent |
| 4,627,833 A | 12/1986 | Cook |
| 4,704,909 A | 11/1987 | Grahn et al. |
| 4,713,051 A | 12/1987 | Steppe et al. |
| 4,758,238 A | 7/1988 | Sundblom et al. |
| 4,773,897 A | 9/1988 | Scheller et al. |
| 4,787,070 A * | 11/1988 | Suzuki et al. ................. 367/140 |
| 4,790,816 A | 12/1988 | Sundblom et al. |
| 4,798,850 A | 1/1989 | Brown |
| 4,842,584 A * | 6/1989 | Pastrone ....................... 604/505 |
| 5,078,149 A * | 1/1992 | Katsumata et al. ........... 600/459 |
| 5,165,412 A * | 11/1992 | Okazaki ....................... 600/439 |
| 5,265,614 A * | 11/1993 | Hayakawa et al. ........... 600/459 |
| 5,267,956 A | 12/1993 | Beuchat |
| 5,273,517 A * | 12/1993 | Barone et al. .................. 494/37 |
| 5,282,787 A | 2/1994 | Wortrich |
| 5,364,342 A | 11/1994 | Beuchat et al. |
| 5,463,906 A * | 11/1995 | Spani et al. ................ 73/861.27 |
| 5,499,969 A | 3/1996 | Beuchat et al. |

(Continued)

FOREIGN PATENT DOCUMENTS

CA 2127039 3/1996

(Continued)

OTHER PUBLICATIONS

Shigeyuki, I; Bibliographic data: JP2004257738 (A); abstract only; espacenet.com; 1 page, Publication Date: Sep. 16, 2004.

(Continued)

*Primary Examiner* — Theodore Stigell
*Assistant Examiner* — Andrew Gilbert
(74) *Attorney, Agent, or Firm* — W. David Lee

(57) ABSTRACT

An elastomeric acoustic coupler formed by molding a thermoplastic or silicone rubber into a recess of a surgical cassette housing. The coupling has a raised pad to aid in the removal of all air between the transducer and the fluid conduit, and to provide an efficient transmission of an ultrasound signal into the fluid conduit.

5 Claims, 6 Drawing Sheets

U.S. PATENT DOCUMENTS

| | | | |
|---|---|---|---|
| 5,514,102 A | 5/1996 | Winterer et al. | |
| 5,746,241 A | 5/1998 | Stedman | |
| 5,747,824 A | 5/1998 | Jung et al. | |
| 6,039,694 A | 3/2000 | Larson et al. | |
| 6,098,466 A * | 8/2000 | Shkarlet | 73/861.25 |
| 6,171,280 B1 | 1/2001 | Imazu et al. | |
| 6,203,528 B1 * | 3/2001 | Deckert et al. | 604/131 |
| 6,217,530 B1 * | 4/2001 | Martin et al. | 601/2 |
| 6,277,076 B1 * | 8/2001 | Morris et al. | 600/449 |
| 6,315,741 B1 * | 11/2001 | Martin et al. | 601/3 |
| 6,330,831 B1 * | 12/2001 | Lynnworth et al. | 73/861.28 |
| 6,349,599 B1 * | 2/2002 | Lynnworth et al. | 73/644 |
| 6,511,454 B1 | 1/2003 | Nakao et al. | |
| 6,517,487 B1 * | 2/2003 | Mazess et al. | 600/449 |
| 6,554,822 B1 | 4/2003 | Holschneider et al. | |
| 6,599,277 B2 | 7/2003 | Neubert | |
| 6,715,366 B2 | 4/2004 | Ohnishi | |
| 6,820,500 B2 * | 11/2004 | Wilda | 73/861.29 |
| 6,908,451 B2 | 6/2005 | Brody et al. | |
| 7,062,972 B2 * | 6/2006 | Hill | 73/632 |
| 7,168,930 B2 | 1/2007 | Cull et al. | |
| 7,194,919 B2 * | 3/2007 | Shkarlet et al. | 73/861.18 |
| 7,289,914 B2 * | 10/2007 | Hishida et al. | 702/39 |
| 7,392,144 B2 | 6/2008 | Sorensen et al. | |
| 2002/0108450 A1 | 8/2002 | Ohnishi | |
| 2003/0101826 A1 | 6/2003 | Neubert | |
| 2003/0190244 A1 | 10/2003 | Davis et al. | |
| 2003/0195420 A1 * | 10/2003 | Mendlein et al. | 600/437 |
| 2004/0039431 A1 | 2/2004 | Machold et al. | |
| 2004/0050154 A1 | 3/2004 | Machold et al. | |
| 2004/0102707 A1 * | 5/2004 | Murkin | 600/459 |
| 2004/0254469 A1 * | 12/2004 | Shkarlet et al. | 600/459 |
| 2005/0016281 A1 * | 1/2005 | Hill | 73/632 |
| 2005/0215901 A1 * | 9/2005 | Anderson et al. | 600/445 |
| 2005/0241411 A1 * | 11/2005 | Hishida et al. | 73/861.25 |
| 2005/0245888 A1 | 11/2005 | Cull | |
| 2006/0009818 A1 * | 1/2006 | Von Arx et al. | 607/60 |
| 2006/0235303 A1 * | 10/2006 | Vaezy et al. | 600/459 |
| 2007/0005030 A1 | 1/2007 | Hopkins et al. | |
| 2007/0073068 A1 | 3/2007 | Quaedflieg et al. | |
| 2007/0107490 A1 | 5/2007 | Artsyukhovich et al. | |
| 2007/0219494 A1 | 9/2007 | Gao et al. | |
| 2007/0232990 A1 * | 10/2007 | Hopkins et al. | 604/30 |
| 2007/0244427 A1 | 10/2007 | Nazarifar | |
| 2008/0097284 A1 * | 4/2008 | Gao et al. | 604/30 |
| 2009/0232991 A1 * | 9/2009 | Wang et al. | 427/294 |

FOREIGN PATENT DOCUMENTS

| | | |
|---|---|---|
| EP | 1840534 B1 | 9/2009 |
| EP | 1840533 B1 | 9/2010 |
| JP | 2005192890 A | 7/2005 |
| WO | 199318802 A1 | 9/1993 |
| WO | 03047652 A1 | 6/2003 |
| WO | 2007117781 A2 | 10/2007 |

OTHER PUBLICATIONS

Neubert, W.; Bibliographic data: JP2005515806 (T); abstract only; espacenet.com; 1 page, Publication date: Jun. 2, 2005.

* cited by examiner

NON-INVASIVE FLOW MEASUREMENT

This application is a continuation-in-part of U.S. application Ser. No. 11/391,748, filed Mar. 29, 2006, entitled "Surgical System Having a Cassette With An Acoustic Coupling."

FIELD OF THE INVENTION

The present invention relates to an ultrasonic flow sensor, and more particularly, to a surgical system and cassette having an ultrasonic flow sensor.

DESCRIPTION OF THE RELATED ART

Conventional ophthalmic surgical instrument systems use vacuum to aspirate the surgical site and positive pressure to irrigate the site. Typically, a cassette is serially connected between the means used to generate pressure and the surgical instrument. The use of cassettes with surgical instruments to help manage irrigation and aspiration flows at a surgical site is well known. U.S. Pat. Nos. 4,493,695 and 4,627,833 (Cook), U.S. Pat. No. 4,395,258 (Wang, et al.), U.S. Pat. No. 4,713,051 (Steppe, et al.), U.S. Pat. No. 4,798,850 (DeMeo, et al.), U.S. Pat. Nos. 4,758,238, 4,790,816 (Sundblom, et al.), and U.S. Pat. No. 5,267,956 (Beuchat), U.S. Pat. No. 5,364,342 (Beuchat) and U.S. Pat. No. 5,747,824 (Jung, et al.) all disclose ophthalmic surgical cassettes with or without tubes, and they are incorporated in their entirety by this reference. Aspiration fluid flow rate, pump speed, vacuum level, irrigation fluid pressure, and irrigation fluid flow rate are some of the parameters that require precise control during ophthalmic surgery.

Prior art devices have used pressure sensors in the aspiration and irrigation lines and calculated fluid flow rates based on the sensed pressure. In the past, measuring of fluid pressures in surgical cassettes has been very precise and as the resistance in the fluid paths is known, fluid flow rates can be calculated reliably from fluid pressure. Recent improvements in the reliability of ultrasonic flow sensors, however, have now made it possible to non-invasively measure fluid flow accurately.

For example, one ultrasonic flow sensor disclosed in U.S. Pat. No. 6,098,466 (Shkarlet) discloses a flow sensor capable of accurately measuring fluid flow in vessels or tubes having decreased sensitivity to flow distribution non-uniformities and decreased overall size by employing multiple angled reflector surfaces which cause incident ultrasonic waves from one or more ultrasonic transducers to pass through the flow volume multiple times and in multiple directions without changing the planar orientation of the ultrasound waves. The wave paths resulting from the multiple reflections and multi-directional illumination of the flow volume decreases the probe's size and sensitivity to spatial distribution non-uniformities. The multiple angled reflector surfaces also permit the transmitting and receiving ultrasonic transducers to be placed close to one another, thereby reducing the overall probe size and making them particularly useful for incorporation in the relatively small fluid flow cassette used in ophthalmic surgery. In order for an ultrasonic flow sensor to work, the transducer must be acoustically coupled to the tubing in which the fluid is flowing so that any air located between the transducer and the tubing is removed. Prior art flow sensors generally use an acoustic gel, such as a high water content hydrogel material, to accomplish the acoustic coupling. When the acoustic coupling needs to be used in connection with a surgical cassette installed within a surgical console, sterility and cleanliness are of concern, making an acoustic gel less desirable than an acoustic coupling that is formed as part of the cassette or the console and that requires no gel.

Canadian Patent Application No. 2,127,039 A1 describes an elastomer for use as an acoustic coupler for ultrasonic devices. As described in this patent application, the difficulty with independently formed elastomeric acoustic couplers is providing intimate contact between the ultrasound transducer and the elastomer so that no air voids are present at the interface. The solution described in this patent application is an elastomer that is extremely soft and flexible and acoustically transparent. These properties allow the use of relatively thick couplers that may be easily compressed by the transducer, thereby providing greater and firmer contact between the transducer and the elastomer. When used in connection with a surgical cassette installed within a surgical console, a preformed elastomeric acoustic coupler must be either attached to the cassette or to the ultrasound transducer located in the console. The use of an adhesive is undesirable because of the possibility of air bubbles at the interface of the elastomeric coupler and the surface to which it is adhered, and the fact that the adhesive may interfere with the transmission of the ultrasound waves. In addition, an adhesive adds additional interfaces in the acoustic path. Each additional interface degrades the acoustic signal and the sensing system reliability, repeatability and sensitivity.

Accordingly, a need continues to exist for a simple, reliable and accurate acoustic coupler that can be used on or with a surgical cassette.

SUMMARY OF THE INVENTION

An acoustic coupler formed by molding an elastomer thermoplastic or silicone rubber into a cavity of a surgical cassette. The elastomeric coupler comprises a peripheral lip and a raised pad for contacting the ultrasound transducer. In the preferred embodiment the raised pad is semi-cylindrical shaped. In alternative embodiments the raised pad may be circular or "bread loaf" shaped. Such a coupler aids in the removal of all air between the transducer and the fluid conduit, and provides an efficient transmission of an ultrasound signal into the fluid conduit. A surgical cassette and a surgical system employing the acoustic coupler are also disclosed.

BRIEF DESCRIPTION OF THE DRAWINGS

For a more complete understanding of the present invention, and for further objects and advantages thereof, reference is made to the following description taken in conjunction with the accompanying drawings in which.

DETAILED DESCRIPTION OF THE PREFERRED EMBODIMENTS

Figure 2:
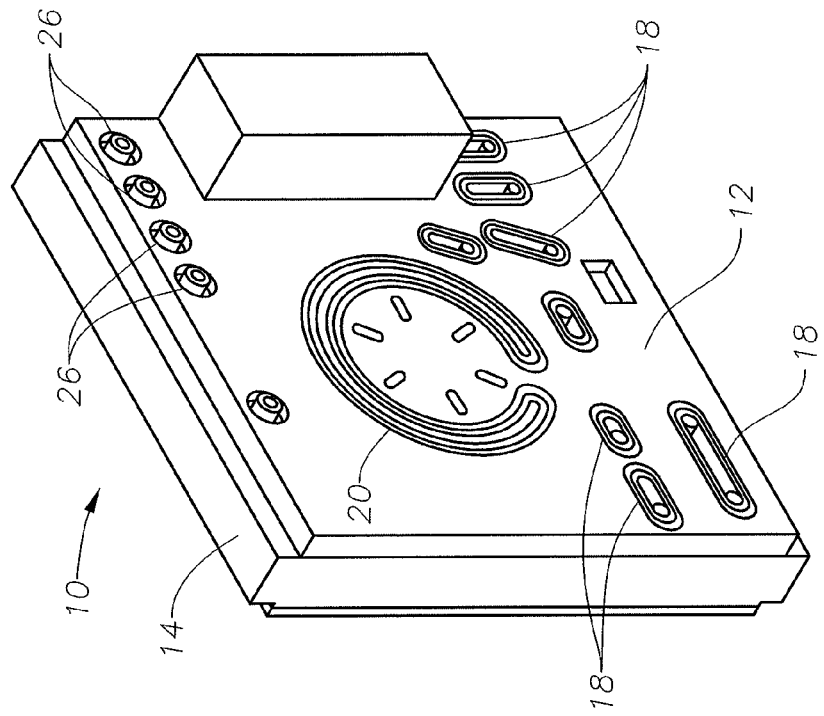
FIG. 2 is a rear perspective view of the cassette of the present invention.
Figure 1:
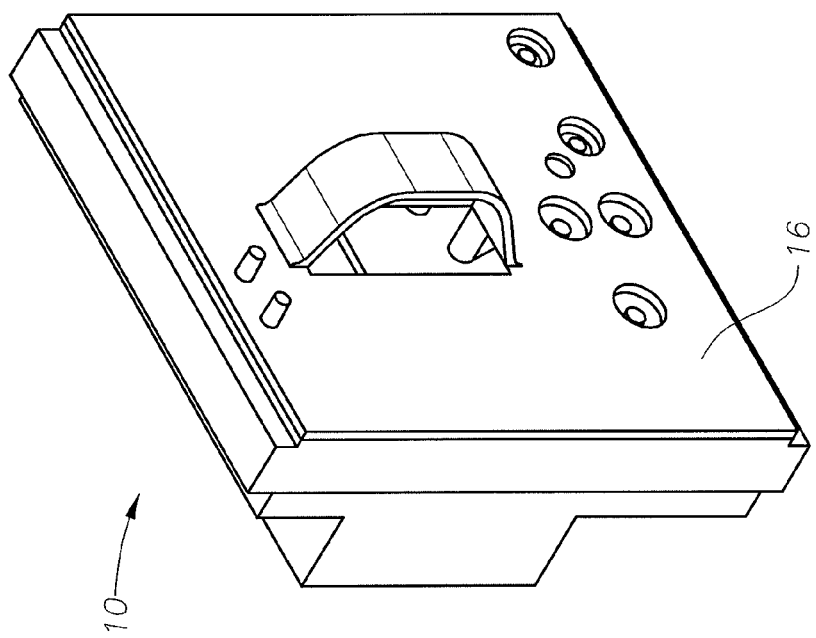
FIG. 1 is a front perspective view of the cassette of the present invention.
Figure 3:
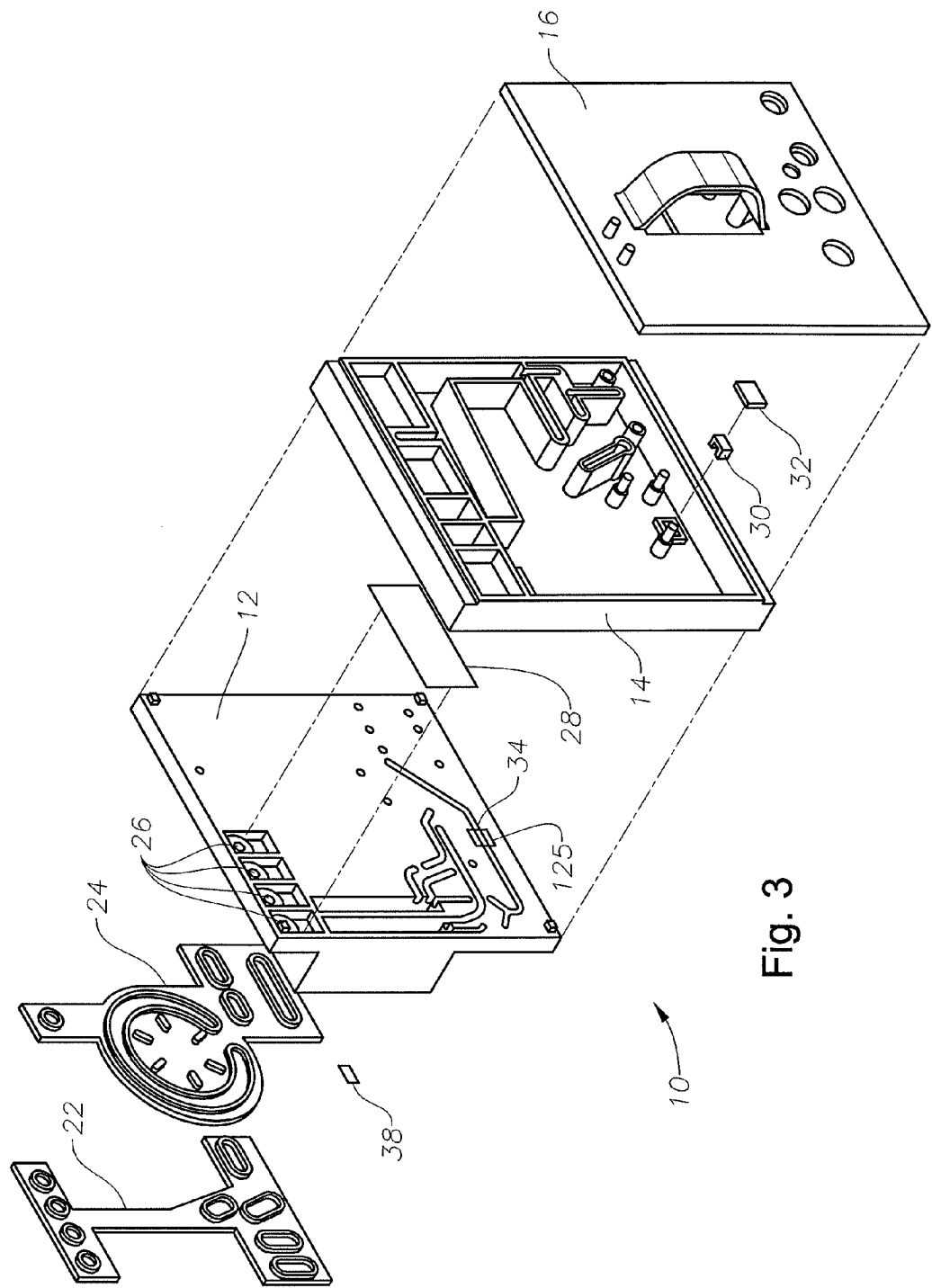
FIG. 3 is an exploded perspective view of the cassette of the present invention.
Figure 4:
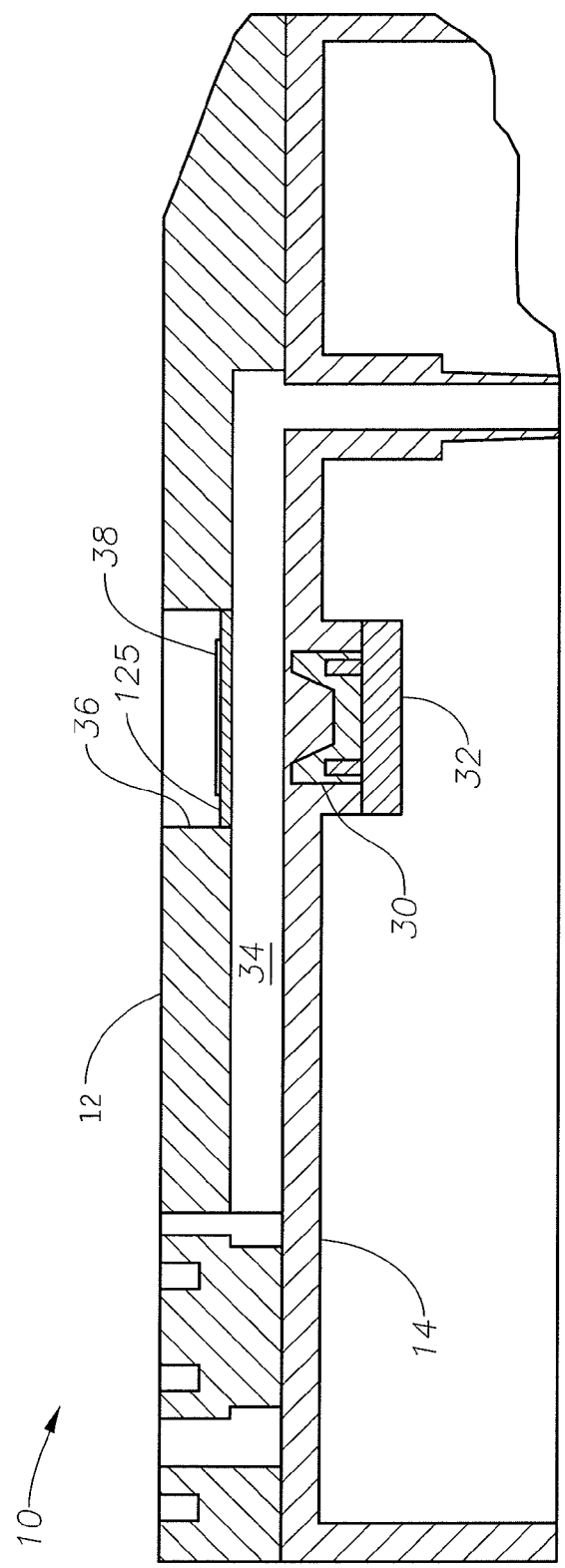
FIG. 4 is a partial cross-sectional view of the cassette of the present invention.
Figure 5:
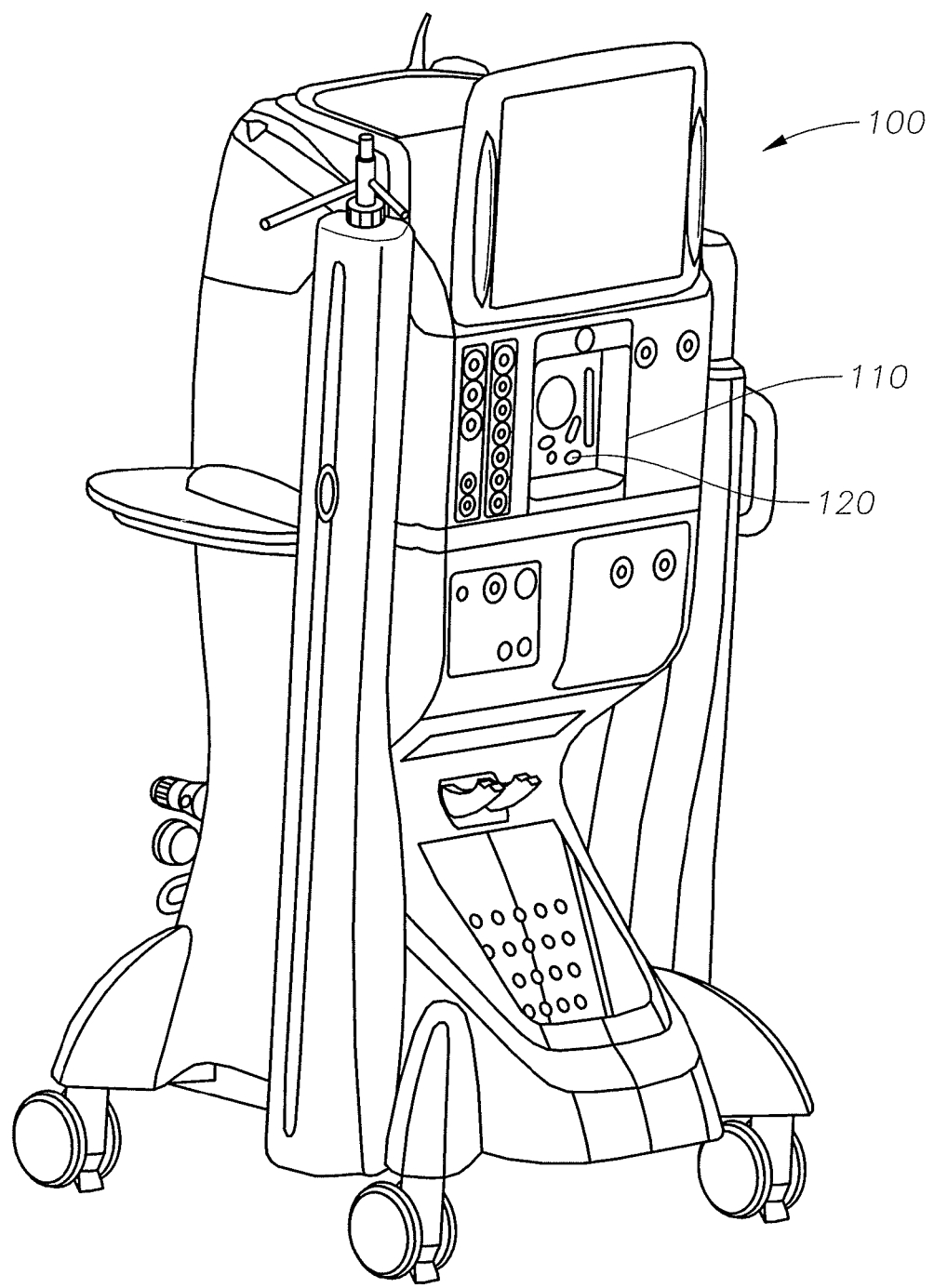
FIG. 5 is a front perspective view of a surgical console that may be used with the cassette of the present invention.

The preferred embodiments of the present invention and their advantages are best understood by referring to FIGS. 1-3 of the drawings, like numerals being used for like and corresponding parts of the various drawings.

Cassette 10 of the present invention generally includes valve plate 12, body 14 and cover 16. Valve plate 12, body 14 and cover 16 may all be formed of a suitable, relatively rigid, thermoplastic. Valve plate 12 contains a plurality of openings 18 and pumping channel 20 that are sealed fluid tight by elastomers 22 and 24, forming a plurality of fluid paths. Ports 26 provide connectors between cassette 10 and surgical console 100 for the various irrigation and aspiration functions of cassette 10. Such functions may require the use of filter 28. Attached to body 14 is ultrasound reflector 30 and reflector cover 32. Acoustic reflector 30 and reflector cover 32 may be molded as one piece and are located on body 14 to align with transmission window 125 in recess 36 along fluid passage 34 formed in valve plate 12 when valve plate 12 is assembled onto body 14 in the manner shown in FIG. 3. Located within recess 36 on valve plate 12 is elastomeric acoustic coupler 38.

Elastomeric acoustic coupler 38 preferably is formed by over molding an elastomeric material, such as a thermoplastic elastomer or silicone rubber, within recess 36 of valve plate 12. Such a construction method eliminates the need for adhesives to attach elastomeric acoustic coupler 38 to valve plate 12 and ensures the removal of any air from between elastomeric acoustic coupler 38 and valve plate 12.

Figure 6:
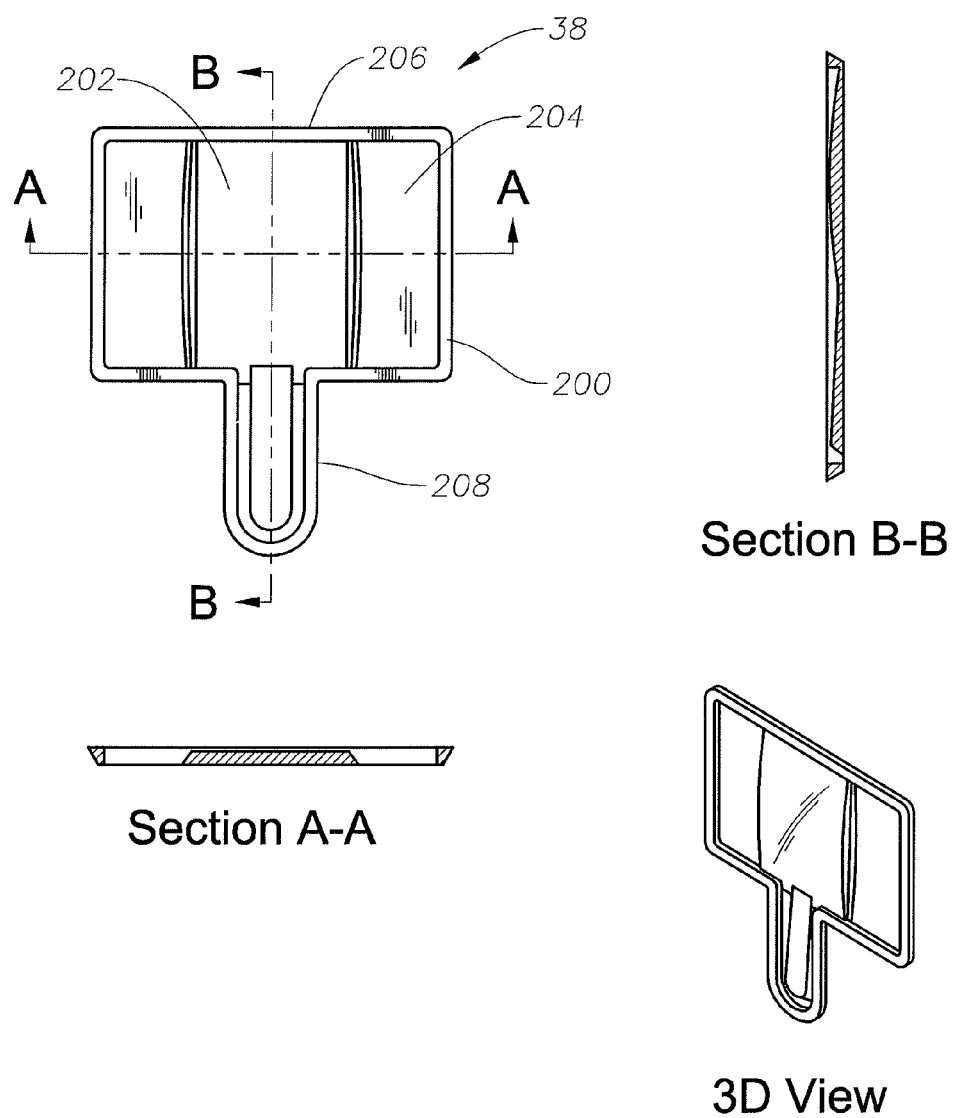
FIG. 6 is a detailed view of the preferred elastomeric acoustic coupler of the present invention showing a semi-cylindrical raised pad.
Figure 7:
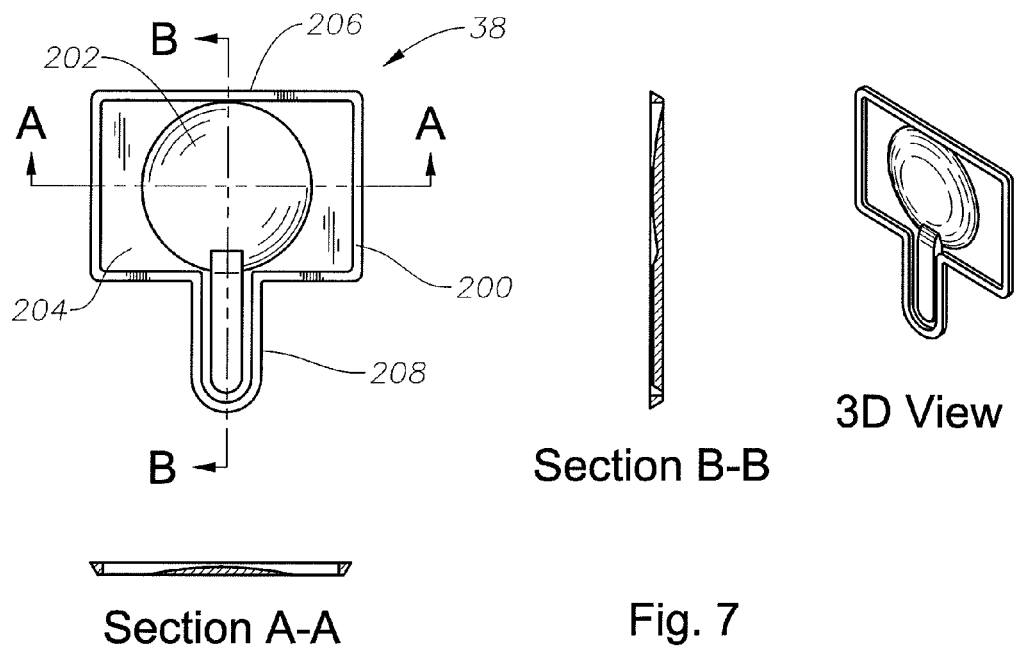
FIG. 7 is a detailed view of an alternative elastomeric acoustic coupler showing a circular raised pad.
Figure 8:
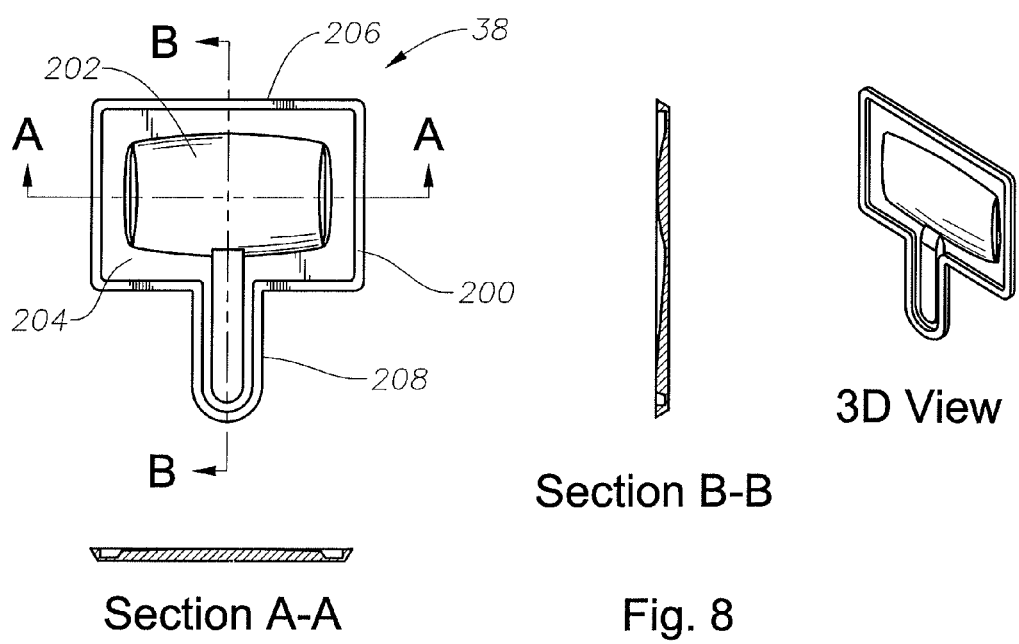
FIG. 8 is a detailed view of an additional alternative elastomeric acoustic coupler showing a "bread loaf" shaped raised pad.

As best illustrated in FIGS. 6-8, elastomeric coupler 38 consists of body 206, and tab 208 extending from the lower edge of body 206. A lip 200 surrounds the periphery of body 206 and tab 208. The height of lip 200 is preferably about 0.037 inches. A raised central pad 202 is disposed in the approximate center of body 206 and extends downward through the center of tab 208. The height of raised pad 202 is preferably between about 0.030 inches and about 0.050 inches. A thin web 204 of elastomeric material connects raised pad 202 to lip 200. FIG. 6 illustrates the most preferred embodiment where the portion of raised pad 202 disposed on body 206 is semi-cylindrical shaped. In this embodiment, the top and bottom edges of raised pad 202 are co-linear with the interior edge of lip 200. FIG. 7 shows an alternative embodiment wherein the portion of raised pad 202 disposed on body 206 is circular shaped. FIG. 8 shows an additional alternative embodiment wherein the portion of raised pad 202 disposed on body 206 is "bread loaf" shaped.

Recess 36 is located adjacent to fluid passage 34 in valve plate 12 and aligned with acoustic reflector 30 and reflector cover 32 when valve plate 12 is assembled on body 14. When cassette 10 is installed in cassette receiving portion 110 of console 100, ultrasound transducer 120 presses against elastomeric acoustic coupler 38, and tightly compresses raised pad 202 between ultrasound transducer 120 and fluid passage 34. This provides an acoustic coupling between transducer 120 and fluid passage 34, thus allowing the use of ultrasound transducer 120 to measure the fluid flow rate in fluid passage 34. It has been discovered that the disclosed shape of raised pad 202, as described hereinabove, greatly increases the effectiveness of coupler 38.

From the above, it may be appreciated that the present invention provides improved apparatus and methods for using acoustic technology to measure flow rates. An invention such as this eliminates the need for the user to apply the couplant material to the device under use, thereby preventing any misuse of the device. Moreover, an invention such as ensures repeatable contact between the transducer, the couplant, and the fluid conduit, and ensures the removal of air between the transducer and the couplant, as well as between the couplant and the fluid conduit. Furthermore, an invention such as this will provide a higher signal to noise ratio for the transmitted ultrasound signal, will require zero settling time of the elastomer material while under pressure by the ultrasound transducer, will provide good sensitivity for ultrasound signal transmission and reception, and will allow high flow rate measurement reliability.

It is believed that the operation and construction of the present invention will be apparent from the foregoing description. While the apparatus and methods shown or described above have been characterized as being preferred, various changes and modifications may be made therein without departing from the spirit and scope of the invention as defined in the following claims.

What is claimed is:

1. An elastomeric acoustic coupler, comprising:
   a body;
   a lip surrounding a periphery of said body, said lip having an interior edge;
   a raised central pad disposed proximate a center of said body, said raised central pad having a top edge, a bottom edge, and a semi-cylindrical shape when viewed from a top view;
   a web connecting said pad to said lip; and
   a tab extending from said body;
   wherein said raised central pad is raised above a level of said web, said top edge and said bottom edge of said raised central pad are co-linear with said interior edge of said lip when viewed from said top view, and said raised central pad has a portion that extends onto said tab.

2. The elastomeric acoustic coupler of claim 1 wherein a height of said lip is approximately 0.037 inches.

3. The elastomeric acoustic coupler of claim 1 wherein height of said pad is between about 0.030 inches and about 0.050 inches.

4. A surgical cassette, comprising:
   a body;
   a valve plate coupled to one side of said body and having a recess formed therein;
   a cover coupled to an opposite side of said body;
   transmission window disposed in said recess;
   a fluid passage defined by said valve plate and said body; and
   an elastomeric acoustic coupler over molded in said recess on said transmission window, said elastomeric acoustic coupler having:
   a body;
   a lip surrounding a periphery of said body, said lip having an interior edge;
   a raised central pad disposed proximate a center of said body, said raised central pad having a top edge, a bottom edge, and a semi-cylindrical shape when viewed from a top view;
   a web connecting said pad to said lip; and
   a tab extending from said body;
   wherein said raised central pad is raised above a level of said web, said top edge and said bottom edge of said raised central pad are co-linear with said interior edge of said lip when viewed from said top view, and said raised central pad has a portion that extends onto said tab.

5. A surgical system, comprising:
   a surgical console, said surgical console having a cassette receiving portion;

an ultrasonic transducer located in said cassette receiving portion of said surgical console, said ultrasonic transducer adapted for measuring fluid flow;

a surgical cassette having a plurality of fluid passages; and an elastomeric acoustic coupler attached to said cassette, said acoustic coupler acoustically coupling said ultrasonic transducer to said cassette when said cassette is installed within said cassette receiving portion of said surgical console so as to allow said ultrasonic transducer to measure fluid flow in at least one of said plurality of fluid passages in said cassette, said elastomeric acoustic coupler having:

a body;

a lip surrounding a periphery of said body, said lip having an interior edge;

a raised central pad disposed proximate a center of said body, said raised central pad having a top edge, a bottom edge, and a semi-cylindrical shape when viewed from a top view;

a web connecting said pad to said lip; and a tab extending from said body;

wherein said raised central pad is raised above a level of said web, said top edge and said bottom edge of said raised central pad are co-linear with said interior edge of said lip when viewed from said top view, and said raised central pad has a portion that extends onto said tab.

* * * * *